US009101389B2

(12) United States Patent
Havel et al.

(10) Patent No.: US 9,101,389 B2
(45) Date of Patent: Aug. 11, 2015

(54) APPARATUS FOR GUIDING THE PLACEMENT OF A SUBCUTANEOUS DEVICE (75) Inventors: William J. Havel, Maple Grove, MN (US); Teresa A. Whitman, Dayton, MN (US); Laurie D. Foerster, Mound, MN (US); Mark T. Marshall, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 983 days.

(21) Appl. No.: 12/431,926

(22) Filed: Apr. 29, 2009

(65) Prior Publication Data

US 2010/0030147 A1 Feb. 4, 2010

Related U.S. Application Data (60) Provisional application No. 61/190,052, filed on Jul. 31, 2008, provisional application No. 61/116,492, filed on Nov. 20, 2008.

(51) Int. Cl.
*A61B 17/34* (2006.01)
*A61N 1/04* (2006.01)
*A61M 5/42* (2006.01)
*A61M 5/158* (2006.01)
(Continued)

(52) U.S. Cl.
CPC .......... *A61B 17/3468* (2013.01); *A61N 1/046* (2013.01); *A61B 17/3462* (2013.01); *A61B 17/3472* (2013.01); *A61B 2017/0003* (2013.01); *A61B 2017/00026* (2013.01); *A61B 2017/00561* (2013.01); *A61B 2017/306* (2013.01); *A61B 2017/320044* (2013.01); *A61B 2017/320056* (2013.01); *A61M 5/425* (2013.01); *A61M 5/427* (2013.01); *A61M 2005/1586* (2013.01); *A61N 1/0504* (2013.01)

(58) Field of Classification Search
CPC .......... A61B 17/3462; A61B 17/3468; A61B 17/3472; A61B 2017/00561; A61B 2017/0003; A61B 2017/320056; A61B 2017/00026; A61B 2017/320044; A61B 2017/306; A61B 2017/3492; A61N 1/046; A61N 1/0504; A61M 5/425; A61M 5/427; A61M 2005/1585; A61M 2005/1586
USPC .................................. 604/115–117; 606/129
See application file for complete search history.

(56) References Cited

U.S. PATENT DOCUMENTS 2,008,340 A * 7/1935 Salvati et al. ................. 604/174
3,515,129 A 6/1970 Truhan
(Continued)

FOREIGN PATENT DOCUMENTS

DE 19713266 A1 10/1998
DE 202006011664 U1 11/2006
(Continued)

OTHER PUBLICATIONS

(PCT/US2009/050185) PCT Notification of Transmittal of the International Search Report and the Written Opinion of the International Searching Authority.

*Primary Examiner* — Nathan R Price
(74) *Attorney, Agent, or Firm* — Michael C. Soldner (57) ABSTRACT

An apparatus for guiding the placement of a subcutaneous device that includes a strap having an indentation configured for a fold of skin and fat layer to be positioned within the indentation as the subcutaneous device is advanced to a desired implantation site.

15 Claims, 13 Drawing Sheets

(51) Int. Cl.
*A61B 17/00* (2006.01)
*A61B 17/30* (2006.01)
*A61B 17/32* (2006.01)
*A61N 1/05* (2006.01)

(56) References Cited

U.S. PATENT DOCUMENTS

| | | | |
|---|---|---|---|
| 4,586,924 A * | 5/1986 | Lanning | 604/115 |
| 4,844,258 A | 7/1989 | Boeckmann et al. | |
| 5,300,106 A | 4/1994 | Dahl et al. | |
| 5,782,841 A | 7/1998 | Ritz et al. | |
| 6,360,750 B1 | 3/2002 | Gerber et al. | |
| 6,652,487 B1 * | 11/2003 | Cook | 604/115 |
| 6,671,554 B2 | 12/2003 | Gibson et al. | |
| 7,025,760 B2 | 4/2006 | Miller et al. | |
| 7,092,765 B2 | 8/2006 | Geske et al. | |
| 7,186,214 B2 | 3/2007 | Ness | |
| 7,192,413 B2 * | 3/2007 | Kraus et al. | 604/9 |
| 7,218,970 B2 | 5/2007 | Ley et al. | |
| 2004/0204728 A1 | 10/2004 | Haefner | |
| 2004/0204734 A1 | 10/2004 | Wagner et al. | |
| 2004/0204735 A1 | 10/2004 | Shiroff et al. | |
| 2004/0260370 A1 | 12/2004 | Ley et al. | |
| 2006/0122676 A1 | 6/2006 | Ko et al. | |
| 2006/0173474 A1 | 8/2006 | Wellman et al. | |
| 2006/0211987 A1 * | 9/2006 | Williams | 604/116 |
| 2007/0135847 A1 | 6/2007 | Kenknight | |
| 2007/0191920 A1 | 8/2007 | Ley et al. | |
| 2008/0269763 A1 | 10/2008 | Bonde et al. | |

FOREIGN PATENT DOCUMENTS

| | | |
|---|---|---|
| GB | 1078187 A | 8/1967 |
| WO | 9956633 A | 11/1999 |
| WO | 2004089780 A | 10/2004 |
| WO | 2007005297 A | 1/2007 |
| WO | 2007060972 A | 5/2007 |

* cited by examiner

APPARATUS FOR GUIDING THE PLACEMENT OF A SUBCUTANEOUS DEVICE

RELATED APPLICATION

This application claims the benefit of and priority to U.S. Provisional Application Ser. No. 61/190,052, filed Jul. 31, 2008, entitled, "Apparatus for Guiding The Placement of a Subcutaneous Device" and to U.S. Provisional Application Ser. No. 61/116,492, filed Nov. 20, 2008, entitled, "Apparatus for Guiding The Placement of a Subcutaneous Device" the contents of which are incorporated by reference herein in its entirety.

CROSS-REFERENCE TO RELATED APPLICATIONS

Cross-reference is hereby made to the commonly assigned related U.S. Applications, U.S. Pat. application Ser. No. 12/432,028, entitled "MEDICAL DEVICE SYSTEM AND APPARATUS FOR GUIDING THE PLACEMENT OF A SUBCUTANEOUS DEVICE", to Havel et al.; and U.S. Pat. application Ser. No. 12/432,014, entitled "MEDICAL DEVICE SYSTEM AND APPARATUS FOR GUIDING THE PLACEMENT OF A SUBCUTANEOUS DEVICE", to Havel et al.; and U.S. Pat. application Ser. No. 12/432,052, "MEDICAL DEVICE SYSTEM AND APPARATUS FOR GUIDING THE PLACEMENT OF A SUBCUTANEOUS DEVICE", to Havel et al., filed concurrently herewith and incorporated herein by reference in their entireties.

BACKGROUND OF THE INVENTION

A subcutaneous device, such as a coil electrode for an implantable cardioverter-defibrillator (ICD), is typically implanted in a patient while the patient is lying supine on his or her back. The subcutaneous device is implanted using a tunneling tool that provides enough stiffness and pushability to create a space between the subcutaneous and muscular plane. With the patient on his or her back, it is difficult for a physician to maneuver a tunneling tool around the curvature of the posterior axilla to continue tunneling from the axilla to the spine.

There are two major potential problems that a physician may encounter while implanting a subcutaneous device using a tunneling tool. The first problem includes the tunneling tool turning inward between the ribs and into muscle and potentially creating a pneumothorax. The second problem includes the tunneling tool turning outward and potentially puncturing the skin. Some physicians will have a non-sterile scrub nurse put a hand under the patient's back to help guide the tunneling tool and to give the skin support so the tunneling tool does not penetrate the skin. Other physicians will use x-ray or other suitable imaging systems to help guide the tunneling tool.

For these and other reasons, there is a need for the present invention.

SUMMARY OF THE INVENTION

One embodiment provides an apparatus for guiding the placement of a subcutaneous device. The apparatus includes a strap comprising an indentation configured for a fold of skin and fat layer to be positioned within the indentation.

DETAILED DESCRIPTION OF THE INVENTION

Figure 1A:
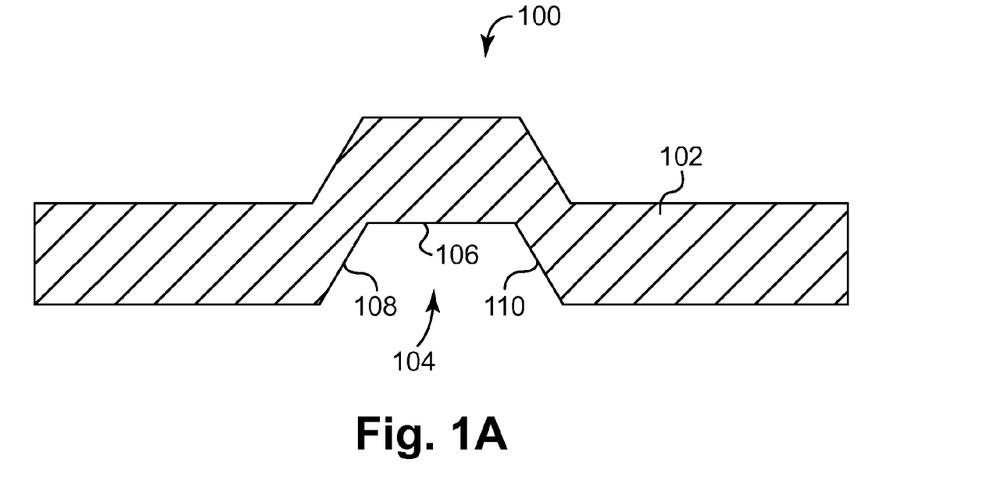
FIG. 1A illustrates a cross-sectional view of one embodiment of an apparatus for guiding the placement of a subcutaneous device.
Figure 1B:
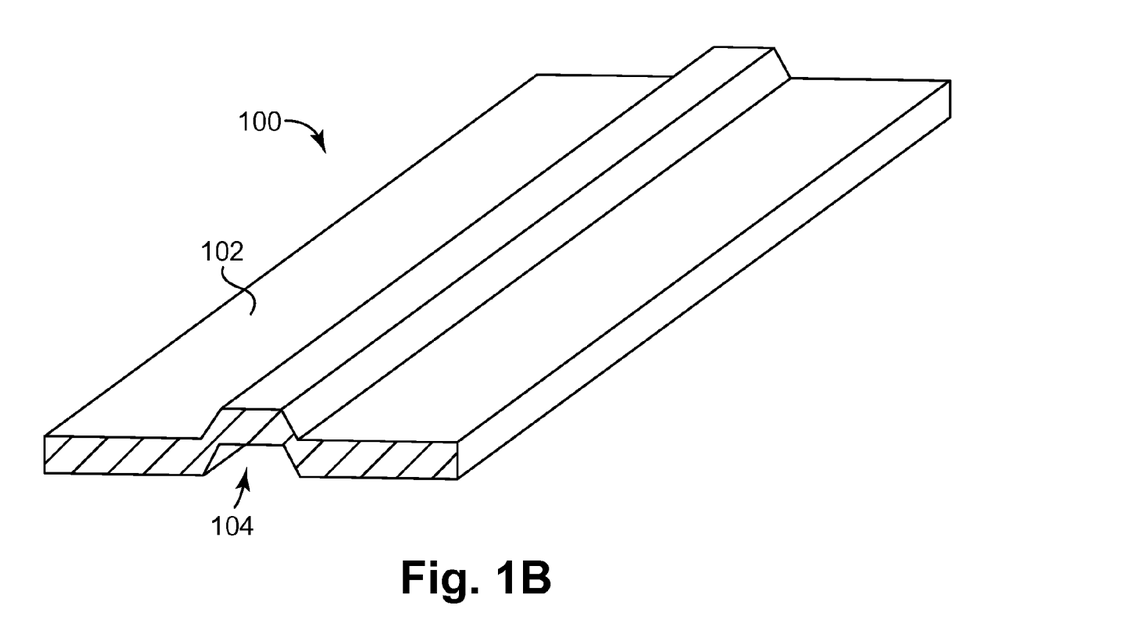
FIG. 1B illustrates a perspective view of one embodiment of an apparatus for guiding the placement of a subcutaneous device.

FIGS. 1A illustrates a cross-sectional view of one embodiment of an apparatus 100 for guiding the placement of a subcutaneous device. FIG. 1B illustrates a perspective view of apparatus 100. Apparatus 100 includes a strap 102 including an indentation 104 formed along the length of strap 102. Indentation 104 includes a base portion 106, a first sidewall portion 108, and a second sidewall portion 110. Second sidewall portion 110 is opposite first sidewall portion 108.

Apparatus 100 is positioned over the appropriate intercostal space from the mid-axilliary line to the spine of a patient. Apparatus 100 is then attached to the patient. Indentation 104 allows a fold of skin and fat layer of the patient to compress into indentation 104 or to be positioned within indentation 104 when the patient lies down on an operating table. Indentation 104 provides a mechanical guide for a tunneling tool during the placement of a subcutaneous device, such as a coil electrode or lead. Indentation 104 also provides for more precise placement of the subcutaneous device compared to typical methods. In addition, apparatus 100 holds the skin taut so that the skin does not fold or snag during tunneling. Apparatus 100 replaces the need to have a hand over the top of the patient's skin or the need to use x-ray or other imaging systems to assist the physician in guiding the tunneling tool.

Strap 102 is made of a semi-stiff material such that strap 102 conforms to a patient's body yet is sufficiently rigid to enable a fold of skin and fat layer of the patient to be compressed into indentation 104 with strap 102 attached to the patient. In one embodiment, strap 102 is made of plastic that has sufficient flex to conform to a patient's body. In another embodiment, strap 102 is made of rubber. In other embodiments, strap 102 is made of other suitable materials or combinations of materials. In one embodiment, strap 102 is approximately 12 to 18 inches long. In one embodiment, strap 102 can be sterilized.

Figure 2:
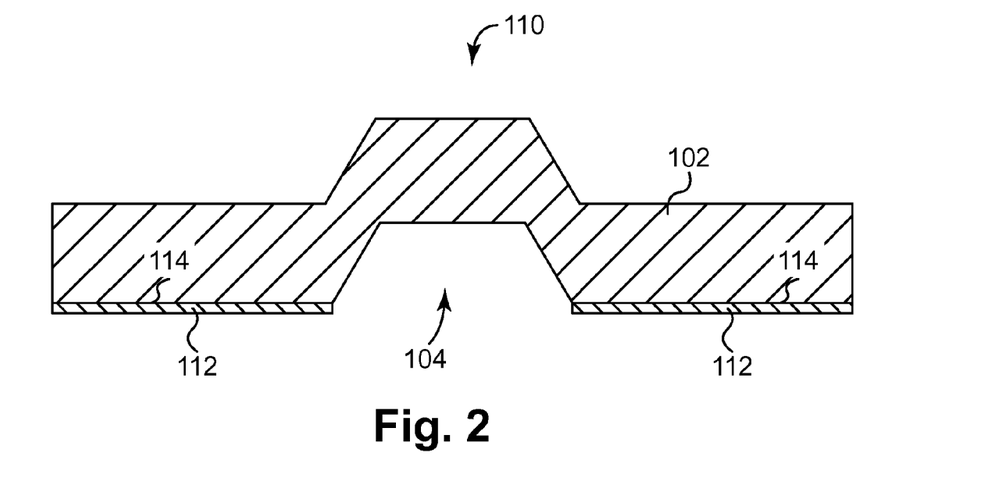
FIG. 2 illustrates a cross-sectional view of another embodiment of an apparatus for guiding the placement of a subcutaneous device.

FIG. 2 illustrates a cross-sectional view of another embodiment of an apparatus 110 for guiding the placement of a subcutaneous device. Apparatus 110 is similar to apparatus 100 previously described and illustrated with reference to FIGS. 1A and 1B, except that apparatus 110 includes adhesive 112. Adhesive 112 is attached to the bottom 114 of strap 102 adjacent to indentation 104. Adhesive 112 is used to attach strap 102 to a patient. In one embodiment, adhesive 112 includes a double sided tape. In other embodiments, adhesive 112 is applied to strap 102, which is then attached to a patient.

Figure 3:
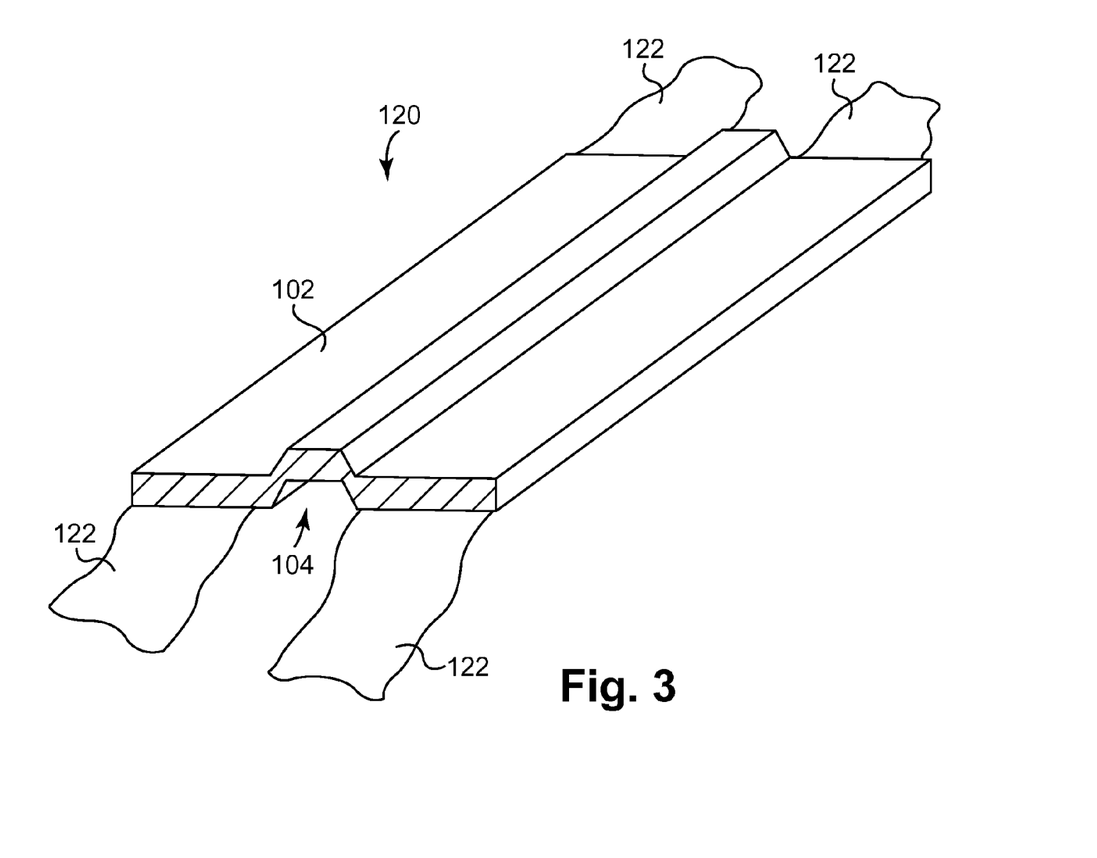
FIG. 3 illustrates a perspective view of another embodiment of an apparatus for guiding the placement of a subcutaneous device.

FIG. 3 illustrates a perspective view of another embodiment of an apparatus 120 for guiding the placement of a subcutaneous device. Apparatus 120 is similar to apparatus 100 previously described and illustrated with reference to FIGS. 1A and 1B, except that apparatus 120 includes bands 122. Bands 122 are attached to strap 102 adjacent to indentation 104. Bands 122 are used to attach strap 102 to a patient by wrapping bands 122 around the patient. In one embodiment, bands 122 are elasticized bands or other suitable bands suitable for attaching strap 102 to a patient.

Figure 4:
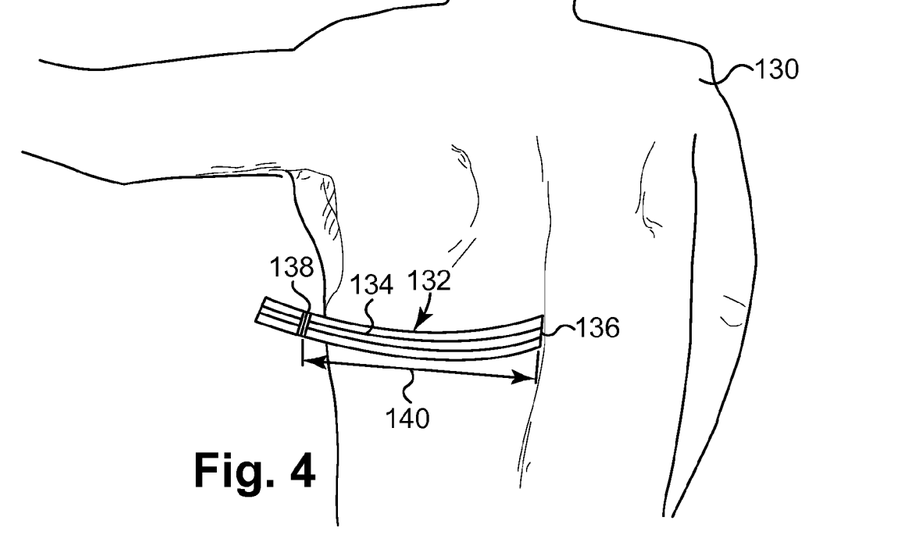
FIG. 4 is a diagram illustrating one embodiment of an apparatus attached to a patient for guiding the placement of a subcutaneous device.

FIG. 4 is a diagram illustrating one embodiment of an apparatus 132 attached to a patient 130 for guiding the placement of a subcutaneous device. Apparatus 132 includes a strap 134 including an indentation similar to apparatus 100 previously described and illustrated with reference to FIGS. 1A and 1B, apparatus 110 previously described and illustrated with reference to FIG. 2, or apparatus 120 previously described and illustrated with reference to FIG. 3.

In one embodiment, strap 134 is attached to patient 130 such that end 136 of strap 134 is at the desired location for the placement of a subcutaneous device. In one embodiment, strap 134 includes a mark or marks 138 for indicating how far a tunneling tool should be inserted to reach the desired location for the placement of a subcutaneous device at end 136 of strap 134. The distance between end 136 of strap 134 and mark or marks 138 is indicated at 140.

Figure 5:
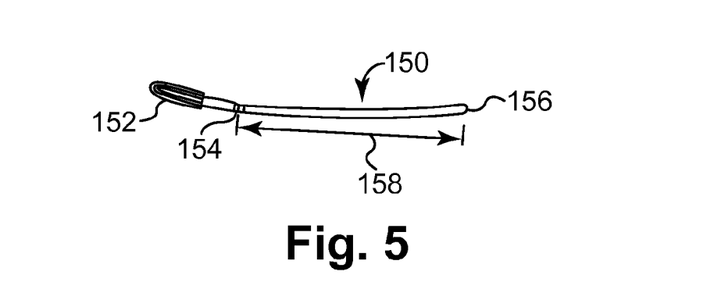
FIG. 5 is a diagram illustrating one embodiment of a tunneling tool.

FIG. 5 is a diagram illustrating one embodiment of a tunneling tool 150. Tunneling tool 150 includes a handle 152 at a proximal end and a tip 156 at a distal end. In one embodiment, tunneling tool 150 includes a mark or marks 154 at the proximal end near handle 152. Mark or marks 154 correspond to mark or marks 138 on strap 134 previously described and illustrated with reference to FIG. 4. The distance between mark or marks 154 and tip 156 of tunneling tool 150 indicated at 158 equals the distance between mark or marks 138 and end 136 of strap 134 indicated at 140. Therefore, by aligning mark or marks 154 on tunneling tool 150 with mark or marks 138 on strap 134, tip 156 of tunneling tool 150 is positioned at end 136 of strap 134 for placing a subcutaneous device at the desired location.

Figure 6A:
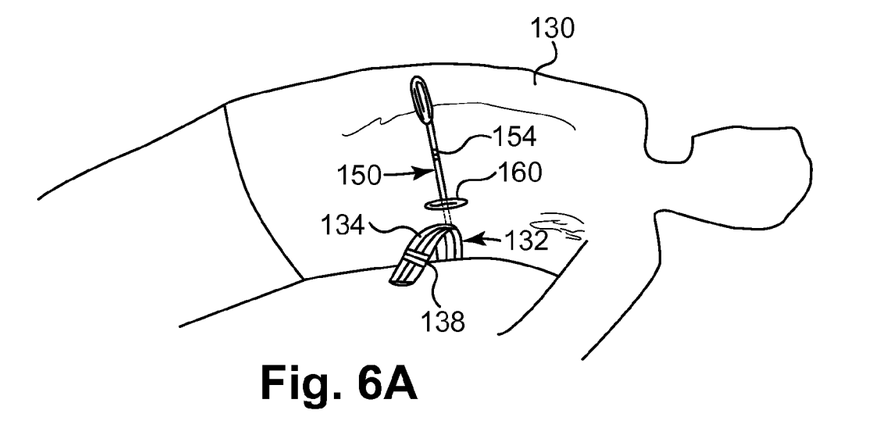
FIG. 6A is a diagram illustrating one embodiment of using the tunneling tool and the apparatus for guiding the placement of a subcutaneous device in a patient.

FIG. 6A is a diagram illustrating one embodiment of using tunneling tool 150 and apparatus 132 for guiding the placement of a subcutaneous device in a patient 130. Apparatus 132 is attached to patient 130 and the patient lies down on an operating table. A physician makes a subcutaneous pocket incision at 160 and inserts tunneling tool 150 into incision 160. As the physician advances tunneling tool 150 using apparatus 132 as a mechanical guide for the tunneling tool, the tunneling tool creates a space between the subcutaneous and muscular plane in patient 130. The physician continues to advance tunneling tool 150 until mark or marks 154 on tunneling tool 150 are aligned with mark or marks 138 on strap 134 indicating that tip 156 of tunneling tool 150 is at the desired location for placing the subcutaneous device.

Figure 6B:
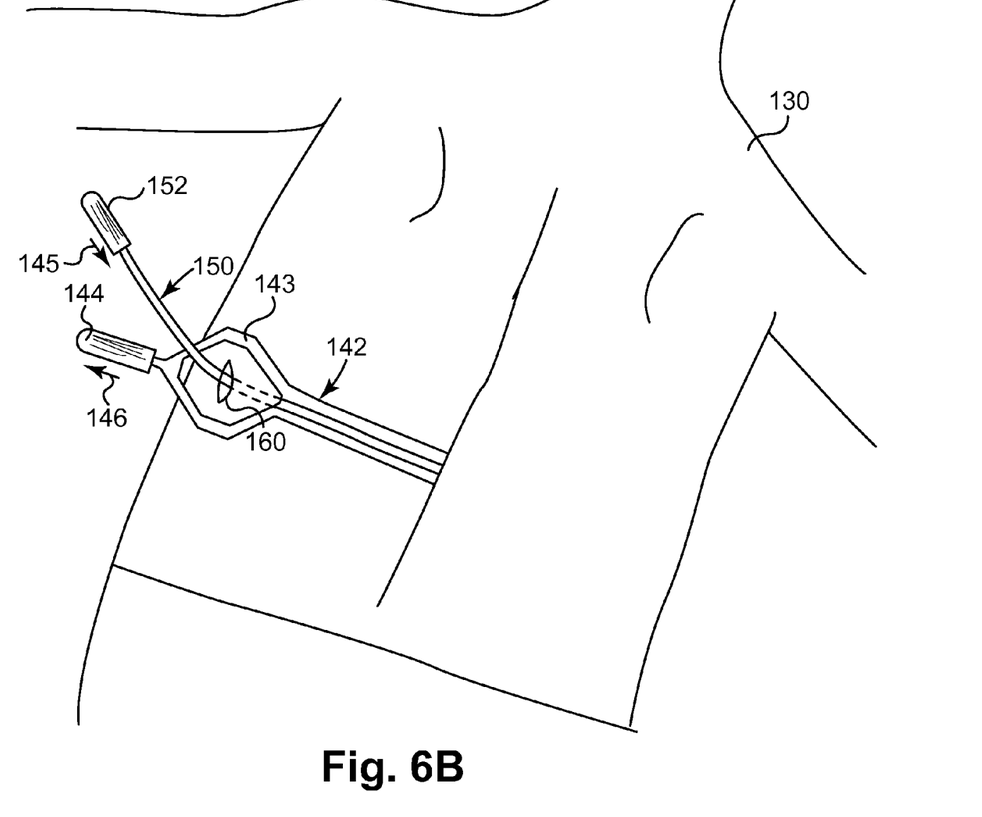
FIG. 6B is a diagram illustrating another embodiment of using the tunneling tool and an apparatus for guiding the placement of a subcutaneous device in a patient.

FIG. 6B is a diagram illustrating another embodiment of using tunneling tool 150 and an apparatus 142 for guiding the placement of a subcutaneous device in a patient 130. In this embodiment, apparatus 142 includes a handle 144, which is attached to the proximal end of the strap via an open frame connection 143. The open frame connection 143 between handle 144 and the strap provides a window through which a physician can access incision 160 and insert tunneling tool 150. As the physician inserts tunneling tool 150 by applying a force on handle 152 as indicated by arrow 145, a counterforce as indicated by arrow 146 is applied to handle 144 such that apparatus 142 keeps the skin of patient 130 taut to make advancement of tunneling tool 150 easier.

Figure 6C:
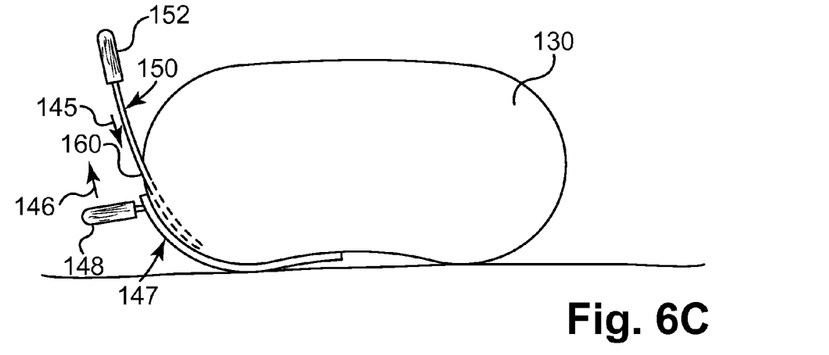
FIG. 6C is a diagram illustrating another embodiment of using the tunneling tool and an apparatus for guiding the placement of a subcutaneous device in a patient.

FIG. 6C is a diagram illustrating another embodiment of using tunneling tool 150 and an apparatus 147 for guiding the placement of a subcutaneous device in a patient 130. In this embodiment, apparatus 147 includes a handle 148, which is directly attached to the proximal end of the strap. In one embodiment, handle 148 is attached to the strap at a 90 degree angle or another suitable angle such that handle 148 does not interfere with handle 152 of tunneling tool 150. As the physician inserts tunneling tool 150 by applying a force on handle 152 as indicated by arrow 145, a counterforce as indicated by arrow 146 is applied to handle 148 such that apparatus 147 keeps the skin of patient 130 taut to make advancement of tunneling tool 150 easier.

Figure 7:
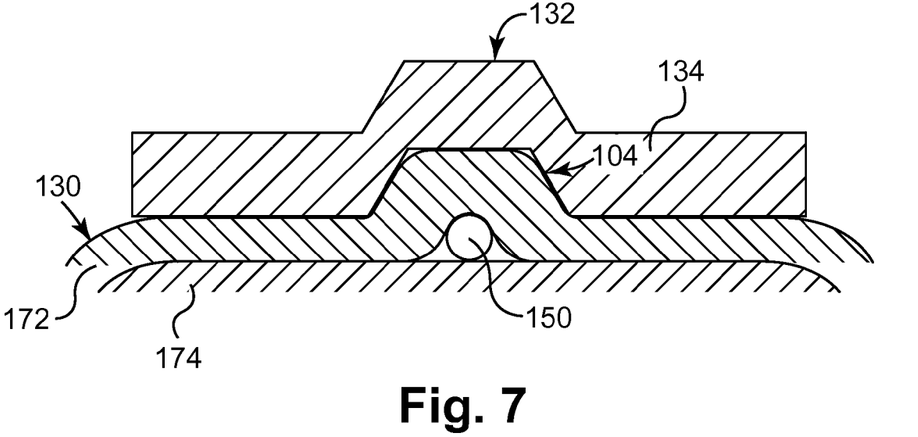
FIG. 7 illustrates a cross-sectional view of one embodiment of using the tunneling tool and the apparatus for guiding the placement of a subcutaneous device in a patient.

FIG. 7 illustrates a cross-sectional view of one embodiment of using tunneling tool 150 and apparatus 132 for guiding the placement of a subcutaneous device in a patient 130. A skin and fat layer or cutaneous tissue 172 of patient 130 is compressed into indentation 104 of strap 134. By using strap 134 as a mechanical guide, tunneling tool 150 creates a space between the skin and fat layer 172 and muscle 174.

Figure 8:
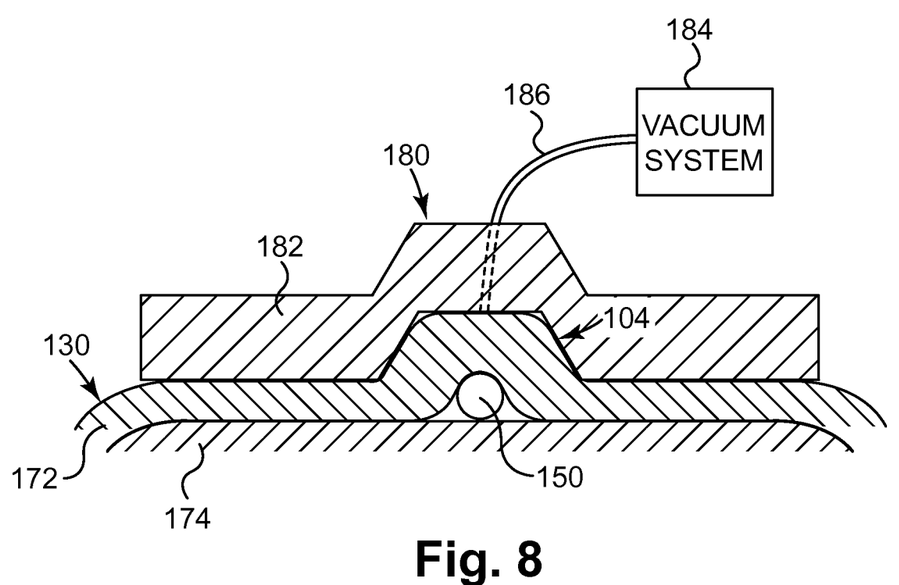
FIG. 8 illustrates a cross-sectional view of another embodiment of using the tunneling tool and an apparatus including a vacuum system for guiding the placement of a subcutaneous device in a patient.

FIG. 8 illustrates a cross-sectional view of another embodiment of using tunneling tool 150 and an apparatus 180 including a vacuum system 184 for guiding the placement of a subcutaneous device in a patient 130. A vacuum system 184 is attached to apparatus 180 through a vacuum line 186. Vacuum line 186 passes through strap 182 to indentation 104. The vacuum pulls the skin upward to be positioned within indentation 104 and holds skin and fat layer 172 in indentation 104. In one embodiment, the vacuum is provided within indentation 104 along the entire length of strap 182 using a network of vacuum lines within strap 182. In one embodiment, the ends of strap 182 are sealed to prevent air outside of strap 182 from entering vacuum system 184.

Figure 9:
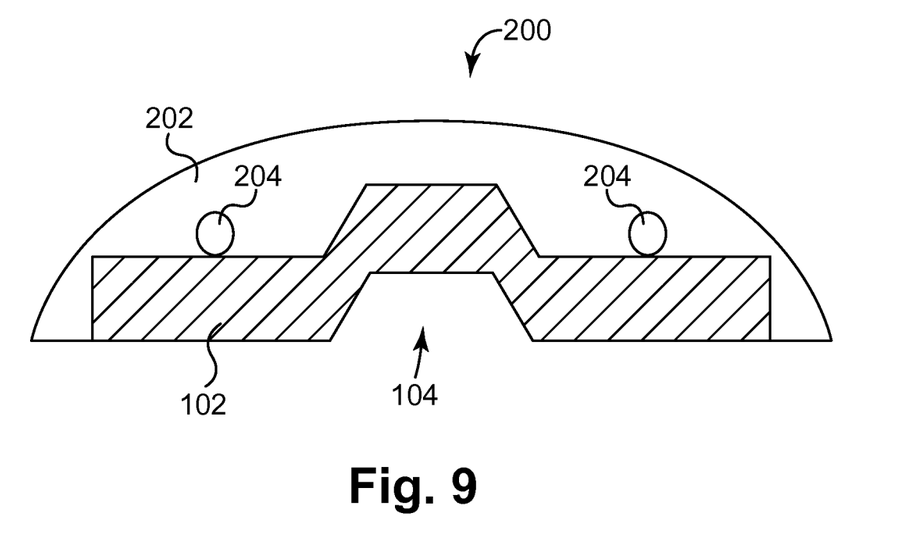
FIG. 9 illustrates a cross-sectional view of another embodiment of an apparatus for guiding the placement of a subcutaneous device.

FIG. 9 illustrates a cross-sectional view of another embodiment of an apparatus 200 for guiding the placement of a subcutaneous device. Apparatus 200 is similar to apparatus 100 previously described and illustrated with reference to FIGS. 1A and 1B, except that apparatus 200 includes additional material 202. In one embodiment, the top and sidewalls of strap 102 are coated with a polymer 202 or other suitable material. Material 202 is selected such that apparatus 200 is smooth to the touch and is slippery to allow a patient to move on an operating table without binding or sticking to the table surface.

In one embodiment, a hollow channel or channels 204 are provided along the length of strap 102 through material 202. In another embodiment, channels 204 are provided through strap 102. After apparatus 200 is attached to a patient, a tunneling tool can be inserted into a channel 204 to shape the tunneling tool to conform to the patient's body prior to inserting the tunneling tool into the patient's body.

Figure 10:
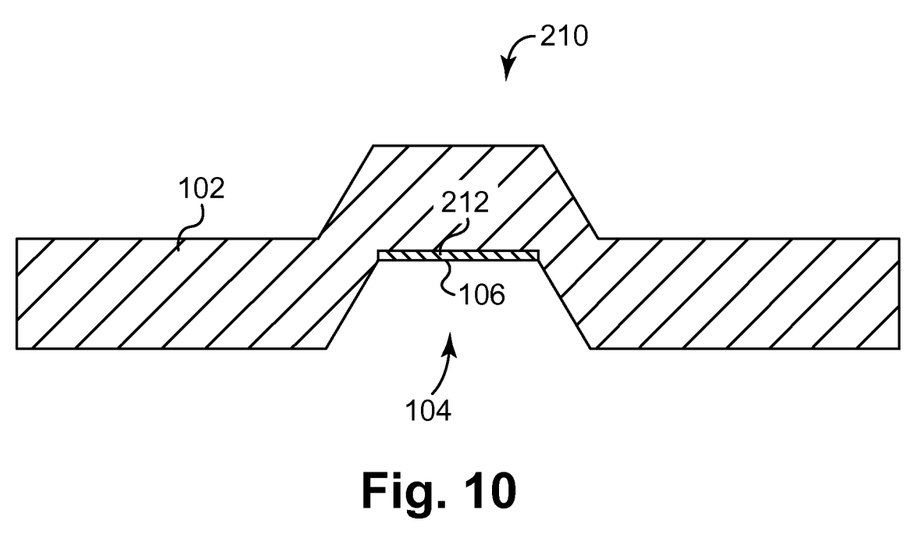
FIG. 10 illustrates a cross-sectional view of another embodiment of an apparatus for guiding the placement of a subcutaneous device.

FIG. 10 illustrates a cross-sectional view of another embodiment of an apparatus 210 for guiding the placement of a subcutaneous device. Apparatus 210 is similar to apparatus 100 previously described and illustrated with reference to FIGS. 1A and 1B, except that apparatus 210 includes a conductive surface 212 along the base portion 106 of indentation 104. Conductive surface 212 provides an indifferent conductor or electrode for an impedance measurement between electrode 212 and the tip of a lead or the tip of a tunneling tool, which provides the active probe for the impedance measurement. In one embodiment, the impedance measurement provides an electrical guide for guiding the tunneling tool during placement of a subcutaneous device. The impedance measurement provides an indication of the depth of the tunneling tool beneath the skin. As the tunneling tool moves toward a patient's skin, the impedance decreases. As the tunneling move toward a patient's muscle, the impedance increases.

Figure 11:
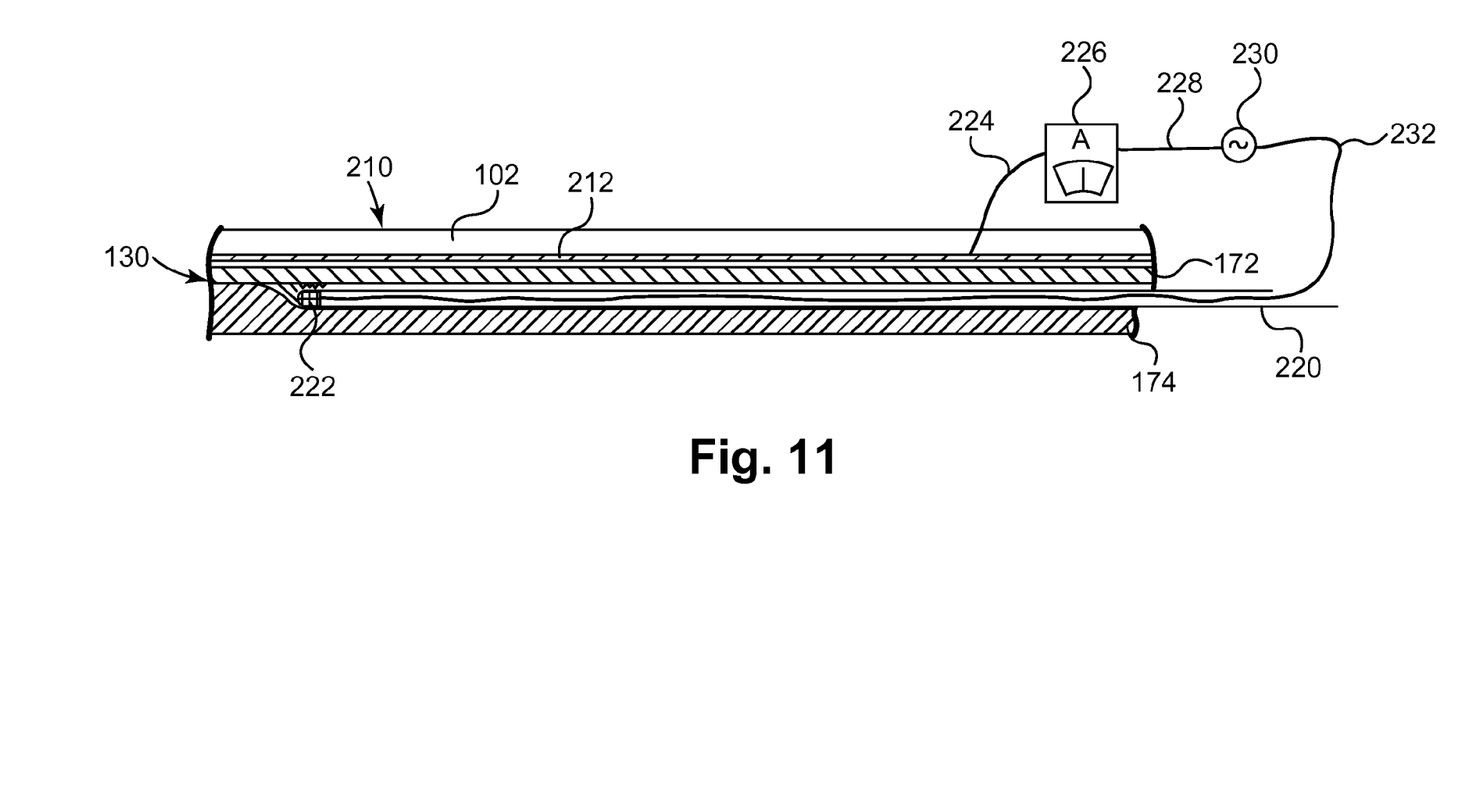
FIG. 11 illustrates a cross-sectional view of another embodiment of using the tunneling tool and the apparatus for guiding the placement of a subcutaneous device in a patient.

FIG. 11 illustrates a cross-sectional view of another embodiment of using a tunneling tool 220 and apparatus 210 for guiding the placement of a subcutaneous device in a patient 130. Apparatus 210 including electrode 212 is attached to a patient 130. In one embodiment, a conductive gel or other suitable material is applied to electrode 212 before attaching apparatus 210 to the patient. Electrode 212 is electrically coupled to one side of an ammeter 226 through signal path 224. The other side of ammeter 226 is electrically coupled to one side of a voltage source 230 through signal path 228. The other side of voltage source 230 is electrically coupled to a tunneling tool electrode 222 through signal path 232. In one embodiment, tunneling tool electrode 222 is the tip of a lead. In another embodiment, tunneling tool electrode 222 is the tip of tunneling tool 220. Signal path 232 passes through the inside of tunneling tool 220 to the tunneling tool electrode 222. Except for the tunneling tool electrode 222, tunneling tool 220 is electrically insulated.

Voltage source 230 provides a voltage between electrode 212 and tunneling tool electrode 222. Ammeter 226 measures the current between electrode 212 and tunneling tool electrode 222. As the impedance between electrode 212 and tunneling tool electrode 222 increases, the current indicated by ammeter 226 between electrode 212 and tunneling tool electrode 222 decreases. As the impedance between electrode 212 and tunneling tool electrode 222 decreases, the current indicated by ammeter 226 between electrode 212 and tunneling tool electrode 222 increases. Therefore, by monitoring the current indicated by ammeter 226, the depth of tunneling tool 220 beneath the patient's skin can be determined. In this embodiment, tunneling tool 220 is in the desired space between cutaneous tissue 172 and muscle 174. As such, the needle of ammeter 226 is centered indicating that tunneling tool 220 is in the desired space. In other embodiments, ammeter 226 is replaced with a digital meter or other suitable monitor for indicating the impedance between electrode 212 and tunneling tool electrode 222.

Figure 12:
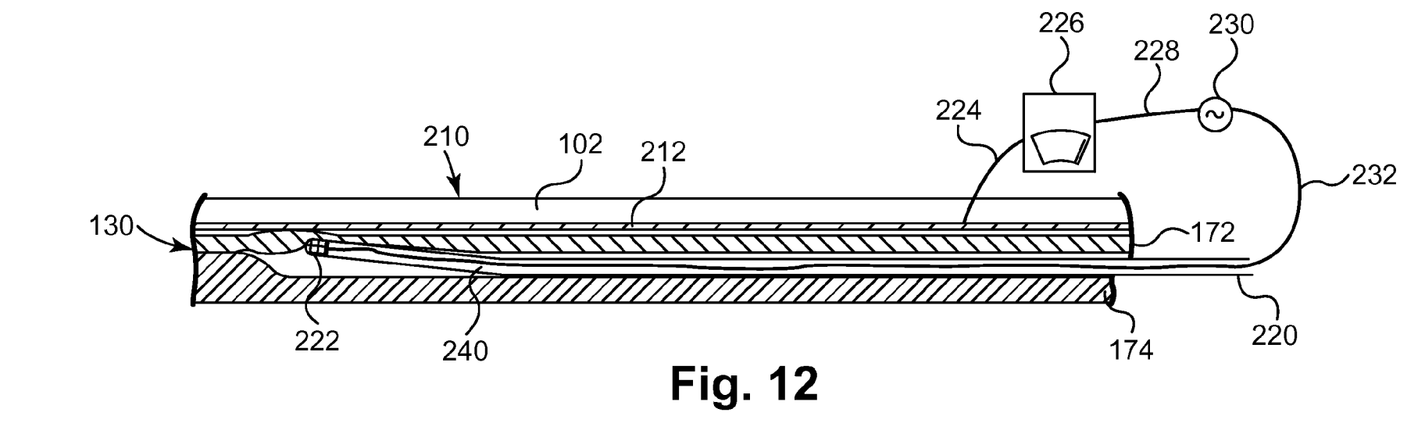
FIG. 12 illustrates a cross-sectional view of another embodiment of using the tunneling tool and the apparatus for guiding the placement of a subcutaneous device in a patient.

FIG. 12 illustrates a cross-sectional view of another embodiment of using tunneling tool 220 and apparatus 210 for guiding the placement of a subcutaneous device in a patient 130. In this embodiment, tunneling tool 220 includes a bend at 240 that is pushing tunneling tool electrode 222 into cutaneous tissue 172 toward the patient's skin. As such, the needle of ammeter 226 is to the right indicating a lower impedance since tunneling tool 220 is approaching the patient's skin. The indication of impedance provided by ammeter 226 can be used to correct the position of tunneling tool 220 before tunneling tool 220 punctures the patient's skin.

Figure 13:
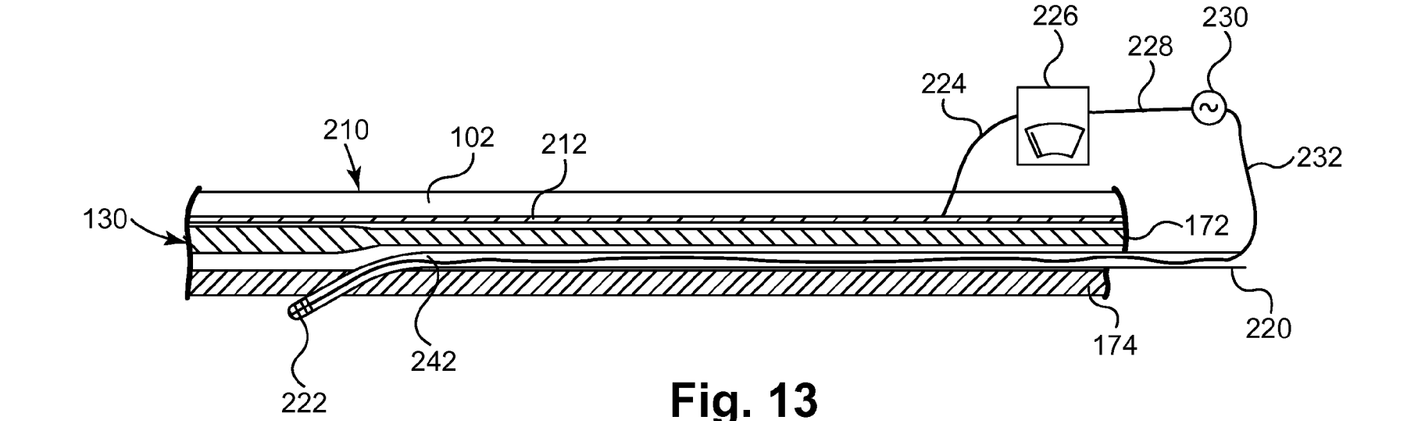
FIG. 13 illustrates a cross-sectional view of another embodiment of using the tunneling tool and the apparatus for guiding the placement of a subcutaneous device in a patient.

FIG. 13 illustrates a cross-sectional view of another embodiment of using tunneling tool 220 and apparatus 210 for guiding the placement of a subcutaneous device in a patient 130. In this embodiment, tunneling tool 220 includes a bend at 242 that is pushing tunneling tool electrode 222 into muscle 174. As such, the needle of ammeter 226 is to the left indicating a higher impedance since tunneling tool 220 is in the patient's muscle 174. The indication of impedance provided by ammeter 226 can be used to correct the position of tunneling tool 220 before tunneling tool 220 creates a pneumothorax.

Figure 14:
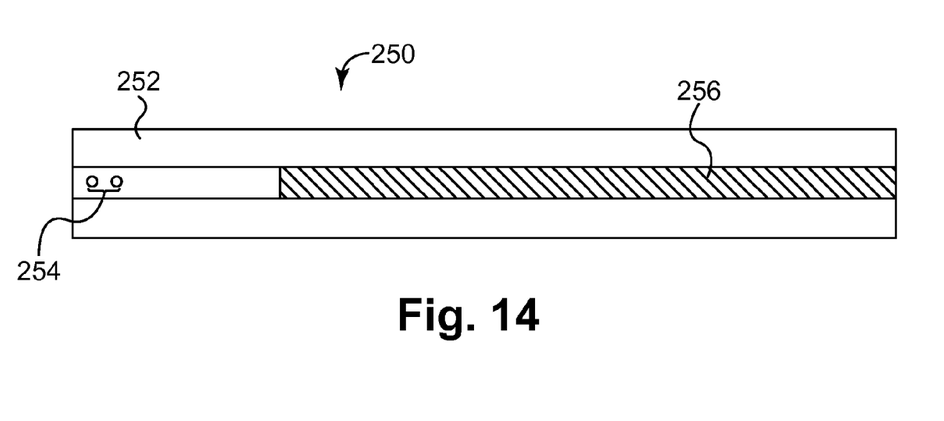
FIG. 14 illustrates a bottom view of another embodiment of an apparatus for guiding the placement of a subcutaneous device.

FIG. 14 illustrates a bottom view of another embodiment of an apparatus 250 for guiding the placement of a subcutaneous device. Apparatus 250 includes a strap 252 including a reference electrode 256 and a bipole electrode 254. Reference electrode 256 is similar to electrode 212 previously described and illustrated with reference to FIG. 10, except that reference electrode 256 does not extend the entire length of strap 252. Reference electrode 256 is used similarly to electrode 212. Bipole electrode 254 is used as a target for positioning the tip of a tunneling tool for the placement of a subcutaneous device.

Figure 15:
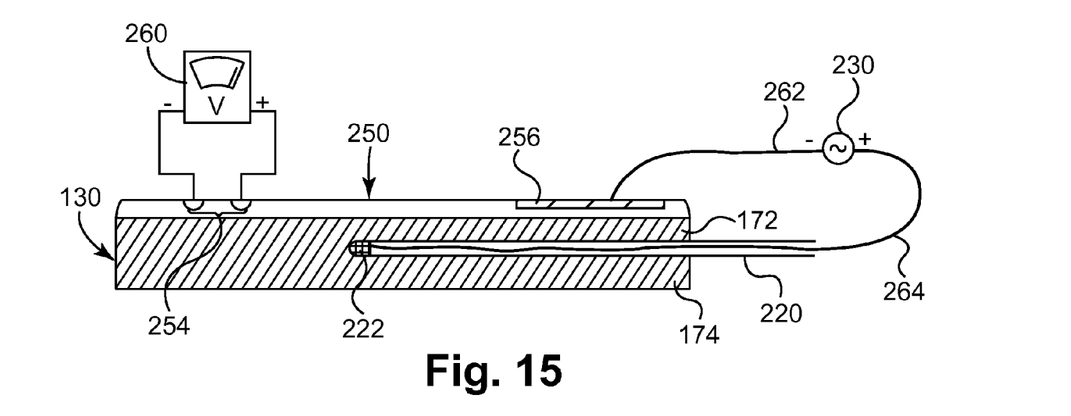
FIG. 15 illustrates a cross-sectional view of another embodiment of using the tunneling tool and the apparatus for guiding the placement of a subcutaneous device in a patient.

FIG. 15 illustrates a cross-sectional view of another embodiment of using tunneling tool 220 and apparatus 250 for guiding the placement of a subcutaneous device in a patient 130. Apparatus 250 including reference electrode 256 and bipole electrode 254 is attached to a patient 130. Apparatus 250 is attached to patient 130 such that bipole electrode 254 is positioned above the desired location for the placement of a subcutaneous device. Reference electrode 256 is electrically coupled to the negative terminal of voltage source 230 through signal path 262. The positive terminal of voltage source 230 is electrically coupled to tunneling tool electrode 222 through signal path 264. Bipole electrode 254 is electrically coupled to a voltmeter 260.

Voltage source 230 provide a voltage between reference electrode 256 and tunneling tool electrode 222. Bipole electrode 254 provides a target location for a subcutaneous device. Voltmeter 260 indicates the position of tunneling tool electrode 222 based on the polarity indicated by the needle of voltmeter 260. In this embodiment, tunneling tool 220 has not yet reached the target location. As such, the needle of voltmeter 260 is to the right indicating a positive polarity. Therefore, the physician should continue to advance tunneling tool 220 toward the target location.

Figure 16:
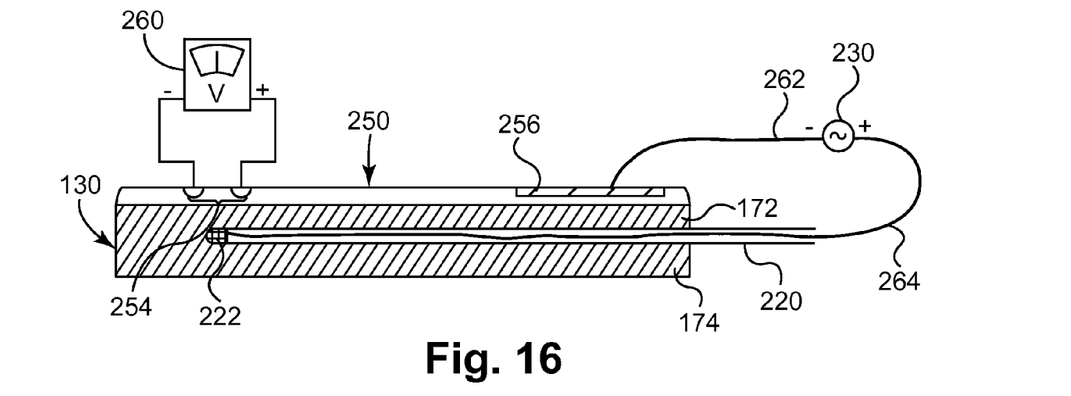
FIG. 16 illustrates a cross-sectional view of another embodiment of using the tunneling tool and the apparatus for guiding the placement of a subcutaneous device in a patient.

FIG. 16 illustrates a cross-sectional view of another embodiment of using tunneling tool 220 and apparatus 250 for guiding the placement of a subcutaneous device in a patient 130. In this embodiment, tunneling tool 220 has reached the target location. As such, the needle of voltmeter 260 is zeroed. Therefore, the physician should stop advancing tunneling tool 220 and place the subcutaneous device at the target location.

Figure 17:
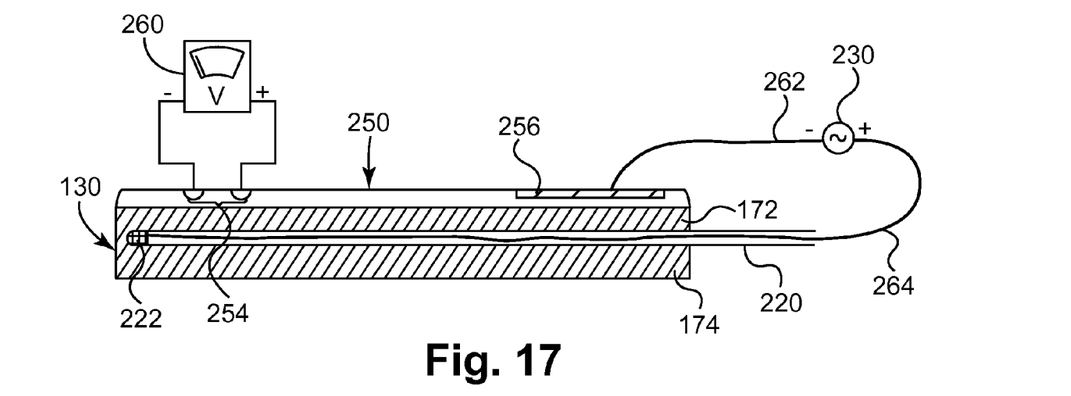
FIG. 17 illustrates a cross-sectional view of another embodiment of using the tunneling tool and the apparatus for guiding the placement of a subcutaneous device in a patient.

FIG. 17 illustrates a cross-sectional view of another embodiment of using tunneling tool 220 and apparatus 250 for guiding the placement of a subcutaneous device in a patient 130. In this embodiment, tunneling tool 220 has past the target location. As such, the needle of voltmeter 260 is to the left indicating a negative polarity. Therefore, the physician should stop advancing tunneling tool 220 and begin retreating tunneling tool 220 toward the target location.

Figure 18:
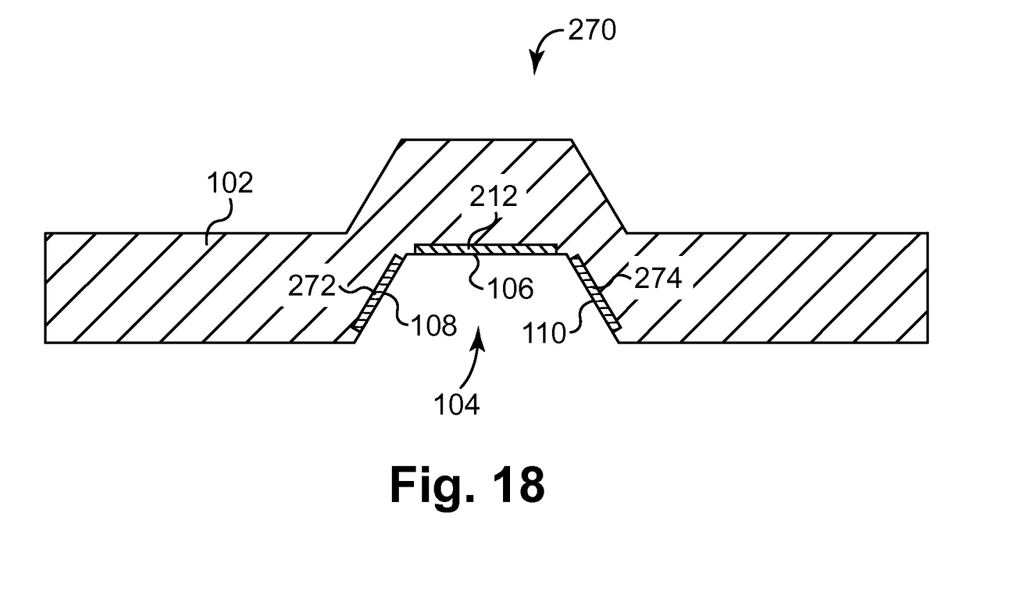
FIG. 18 illustrates a cross-sectional view of another embodiment of an apparatus for guiding the placement of a subcutaneous device.

FIG. 18 illustrates a cross-sectional view of another embodiment of an apparatus 270 for guiding the placement of a subcutaneous device. Apparatus 270 is similar to apparatus 210 previously described and illustrated with reference to FIG. 10, except that apparatus 270 includes a first conductive surface 272 along first sidewall portion 108 of indentation 104 and a second conductive surface 274 along second sidewall portion 110 of indentation 104. Conductive surface 272 provides a first indifferent conductor or first electrode for a first impedance measurement between first electrode 272 and the tip of a lead or the tip of a tunneling tool, which provides the active probe for the impedance measurement. Conductive surface 274 provides a second indifferent conductor or second electrode for a second impedance measurement between second electrode 274 and the tip of a lead or the tip of a tunneling tool.

In one embodiment, the first and second impedance measurements provide an electrical guide for assisting a physician in guiding the tunneling tool during placement of a subcutaneous device. The first and second impedance measurements provide an indication of the lateral position of the tunneling tool between first electrode 272 and second electrode 274. As the tunneling tool moves toward first electrode 272, the impedance between first electrode 272 and the tunneling tool decreases and the impedance between second electrode 274 and the tunneling tool increases. As the tunneling tool moves toward second electrode 274, the impedance between second electrode 274 and the tunneling tool decreases and the impedance between first electrode 272 and the tunneling tool increases.

Embodiments provide an apparatus for assisting a physician in the placement of a subcutaneous device, such as a coil electrode for an implantable cardioverter-defibrillator (ICD) or other suitable subcutaneous device. The apparatus comprises a strap including an indentation for providing a mechanical guide for a tunneling tool. In addition, embodiments provide an electrical guide for assisting a physician in the placement of a subcutaneous device. The electrical guide is based on an impedance measurement or measurements between an electrode on a tunneling tool and an electrode or electrodes on the patient's skin. Embodiments also provide combinations of the mechanical guide and the electrical guide.

Although the present invention has been described with reference to preferred embodiments, workers skilled in the art will recognize that changes can be made in form and detail without departing from the spirit and scope of the present invention.

What is claimed is:

1. An apparatus, comprising:
 a flexible strap comprising an indentation configured for a fold of skin and fat layer to be positioned within the indentation such that placement of a subcutaneous device may be guided subcutaneously along the fold of skin and fat layer positioned within the indentation of the strap; and
 a handle attached to the strap via an open frame connection formed at an end of the strap, the open frame connection being formed to be positioned separate from the indentation to provide a window for access to the indentation of the strap.

2. The apparatus of claim 1, further comprising:
 an adhesive attached to the strap, the adhesive configured for attaching the apparatus to a patient.

3. The apparatus of claim 1, further comprising:
 a band attached to the strap, the band configured for attaching the apparatus to a patient.

4. The apparatus of claim 1, further comprising:
 a channel through the strap, the channel configured for shaping a tunneling tool to conform to a patient's body outside of a patient's body before the tunneling tool is inserted into the patient's body.

5. The apparatus of claim 1, further comprising:
 a vacuum line configured to provide a vacuum within the indentation to pull the fold of skin and fat layer into the indentation.

6. The apparatus of claim 1, further comprising:
 a material covering at least a portion of the strap, the material configured to prevent the apparatus from sticking to a table surface.

7. The apparatus of claim 1, wherein the strap is between 12 to 18 inches long.

8. The apparatus of claim 1, wherein the open frame connection is arranged to attached the handle directly to the strap such that the handle defines one end of the apparatus with the open frame connection interposed between the handle and the end of the strap.

9. The apparatus of claim 1, wherein the handle is positioned relative to the strap such that applying a first force on the handle in a first direction is counter to a second force applied to skin positioned within the open frame connection in a second direction different from the first direction such that the apparatus keeps the skin taut during the application of the first force and the second force simultaneously.

10. A system for placing a subcutaneous device, the system comprising:
 an apparatus including a flexible strap comprising an indentation configured for a fold of skin and fat layer of a patient to be positioned within the indentation such that placement of a subcutaneous device may be guided subcutaneously along the fold of skin and fat layer positioned within the indentation of the strap;
 a tunneling tool configured for insertion into a subcutaneous region of the patient along the indentation of the guide apparatus; and
 a handle attached to the strap via an open frame connection formed at an end of the strap, the open frame connection formed to be positioned separate from the indentation to provide a window for access for insertion of the tunneling tool, wherein the advancing of the tunneling tool through the window positions the fold of skin and fat layer within the indentation.

11. The system of claim 10, wherein the strap comprises a material that conforms to a shape of the patient when attached to the patient.

12. The system of claim 10, wherein the apparatus is configured to be sterilized.

13. The system of claim 10, wherein the strap comprises a first mark,
   wherein the tunneling tool comprises a second mark, and
   wherein the first mark is configured to be aligned with the second mark to indicate a location for placement of the subcutaneous device.

14. The system of claim 10, wherein the open frame connection is arranged to attached the handle directly to the strap such that the handle defines one end of the apparatus with the open frame connection interposed between the handle and the end of the strap.

15. The system of claim 10, wherein the handle is positioned relative to the strap such that applying a first force on the handle in a first direction is counter to a second force applied to skin positioned within the open frame connection by the tunneling tool in a second direction different from the first direction, such that the apparatus keeps the skin taut during insertion of the tunneling tool.

* * * * *